(12) United States Patent
Wang et al.

(10) Patent No.: US 11,998,442 B2
(45) Date of Patent: Jun. 4, 2024

(54) COVERED STENT AND PREPARATION METHOD THEREFOR

(71) Applicant: Shenzhen Lifetech Endovascular Medical Co., Ltd., Shenzhen (CN)

(72) Inventors: Yifei Wang, Shenzhen (CN); Benhao Xiao, Shenzhen (CN)

(73) Assignee: Lifetech Scientific (Shenzhen) Co., Ltd., Shenzhen (CN)

( * ) Notice: Subject to any disclaimer, the term of this patent is extended or adjusted under 35 U.S.C. 154(b) by 42 days.

(21) Appl. No.: 17/418,665

(22) PCT Filed: Dec. 4, 2019

(86) PCT No.: PCT/CN2019/122953
§ 371 (c)(1),
(2) Date: Jan. 20, 2022

(87) PCT Pub. No.: WO2020/134920
PCT Pub. Date: Jul. 2, 2020

(65) Prior Publication Data
US 2022/0257364 A1    Aug. 18, 2022

(30) Foreign Application Priority Data

Dec. 28, 2018  (CN) .......................... 201811626170.5
Dec. 28, 2018  (CN) .......................... 201811626200.2
Dec. 28, 2018  (CN) .......................... 201811628529.2

(51) Int. Cl.
*A61F 2/07*      (2013.01)
*A61F 2/852*     (2013.01)

(52) U.S. Cl.
CPC ................ *A61F 2/07* (2013.01); *A61F 2/852* (2013.01); *A61F 2210/0076* (2013.01); *A61F 2250/0018* (2013.01); *A61F 2250/0036* (2013.01)

(58) Field of Classification Search
CPC .... A61F 2/852; A61F 2/07; A61F 2250/0018; A61F 2250/0036; A61F 2250/0053;
(Continued)

(56) References Cited

U.S. PATENT DOCUMENTS 6,001,125 A    12/1999  Golds et al.
6,517,571 B1 *  2/2003  Brauker ................. A61F 2/06
                                                         623/1.13
(Continued)

FOREIGN PATENT DOCUMENTS

CN        2822554 Y      10/2006
CN        101563049      10/2009
(Continued)

OTHER PUBLICATIONS

Xiao, Lumen Support, Apr. 20, 2016 English translation of CN 105496603 (Year: 2016).*
(Continued)

*Primary Examiner* — Brian E Pellegrino
(74) *Attorney, Agent, or Firm* — Raymond Sun

(57) ABSTRACT

A covered stent comprises a radially compressible inner stent and an outer stent covering the inner stent, the inner stent comprises an inner support skeleton and an inner coating film arranged on the inner support skeleton; and the outer stent covering the inner stent, wherein the outer stent covers at least part of the inner stent, the outer stent comprises an outer support skeleton and an outer coating film arranged on the outer support skeleton, one end of the outer coating film is hermetically connected to the inner coating film, and the resilience of the outer coating film is greater than that of the inner coating film. The inner covering film is relatively soft. The outer covering film can rebound
(Continued)

quickly, the outer stent effectively fills the gap between the inner stent and the wall of the lumen, so as to prevent inner leakage.

8 Claims, 4 Drawing Sheets

(58) Field of Classification Search
CPC ...... A61F 2250/0025; A61F 2250/0051; A61F 2250/0029; A61F 2002/072; A61F 2250/0019
USPC ........................................................ 623/1.35
See application file for complete search history.

(56) References Cited

U.S. PATENT DOCUMENTS

| | | | |
|---|---|---|---|
| 6,729,356 B1 | 5/2004 | Baker et al. | |
| 10,702,370 B2 | 7/2020 | Shu et al. | |
| 2005/0288767 A1* | 12/2005 | Kujawski | A61F 2/07 623/1.13 |
| 2007/0010874 A1 | 1/2007 | Sun | |
| 2014/0121759 A1 | 5/2014 | Cully | |
| 2017/0224467 A1 | 8/2017 | Piccagli | |
| 2017/0239036 A1 | 8/2017 | Cohen et al. | |
| 2017/0290654 A1 | 10/2017 | Sethna | |
| 2018/0280167 A1 | 10/2018 | Folan | |

FOREIGN PATENT DOCUMENTS

| | | | | |
|---|---|---|---|---|
| CN | 204033540 U | | 12/2014 | |
| CN | 105496603 A | | 4/2016 | |
| CN | 105496603 A | * | 4/2016 | ............... A61F 2/07 |
| CN | 105662511 A | | 6/2016 | |
| CN | 107206122 A | | 9/2017 | |
| CN | 109700568 A | | 5/2019 | |
| CN | 109700569 A | | 5/2019 | |
| CN | 109700570 A | | 5/2019 | |
| DE | 102016100774 A1 | * | 7/2017 | ............... A61F 2/852 |
| WO | WO-0051522 A1 | * | 9/2000 | ............... A61F 2/07 |
| WO | WO2008/130848 A1 | | 10/2008 | |
| WO | WO-2012087301 A1 | * | 6/2012 | ............... A61F 2/852 |
| WO | WO-2013123147 A1 | * | 8/2013 | ............... A61F 2/06 |
| WO | WO-2014148122 A1 | * | 9/2014 | ............... A61F 2/07 |
| WO | WO2016/030898 A1 | | 3/2016 | |

OTHER PUBLICATIONS

Kitano et al. Stent, Sep. 25, 2014 English translation of WO 2014/148122 (Year: 2014).*
Bregulla DE 102016100774 english translation (Year: 2017).*
Office Action for corresponding China Application No. 201811626170.5.
Response to Office Action for corresponding China Application No. 201811626170.5.
Notice of Grant dated Apr. 13, 2021 for corresponding China Application No. 201811626170.5.
International Search Report dated Feb. 3, 2020 for corresponding PCT Application No. PCT/CN2019/122953.
Supplementary Search Report dated Jul. 31, 2022 for corresponding European Application No. EP 19 90 4495.
Office Action dated May 2, 2022 for corresponding India Application No. 202127032264.
Search Report for China Application No. 201811626200.2.
Search Report for China Application No. 201811626170.5.
Search Report for China Application No. 201811628529.2.

* cited by examiner

COVERED STENT AND PREPARATION METHOD THEREFOR

TECHNICAL FIELD

The present invention relates to the field of medical equipment, and particularly relates to a covered stent and a preparation method thereof.

BACKGROUND ART

The existing covered stent is generally composed of a metal stent and an anti-leakage covering film, and the material of the covering film may be plastic or polyester. For example, the plastic may be polytetrafluoroethylene (PTFE), and the polyester may be polyethylene terephthalate (PET) or polyurethane (PU). PET and PTFE are two most common materials. The PET covering film is generally fixed to the metal stent by manual sewing, while the PTFE covering film has the characteristics of high elongation, easy deformation, and melting and adhering to each other in a high-temperature state, and such characteristics enable the PTFE material to be able to fix the metal stent in the covering film more easily by means of high-temperature adhesion of inner and outer PTFE films, which has an obvious efficiency advantage compared with manual sewing. Meanwhile, the PTFE material itself has a fibrous microporous structure, so that the PTFE material has better biocompatibility and facilitates the crawling of cells.

SUMMARY OF THE INVENTION

The present disclosure aims to provide a covered stent.
A covered stent comprises a radially compressible inner stent and an outer stent surrounding the inner stent,
the inner stent includes an inner support skeleton and an inner covering film arranged on the inner support skeleton; and
the outer stent covers at least part of the inner stent, the outer stent including an outer support skeleton and an outer covering film arranged on the outer support skeleton, one end of the outer covering film is hermetically connected to the inner covering film, and the resilience of the outer covering film is greater than that of the inner covering film.

According to the covered stent, because the resilience of the inner covering film is smaller, and the straightening force (i.e. the force for restoring from a curved state to a natural state) of the inner stent is smaller, the stimulation of the inner stent to the wall of the lumen can be reduced; in addition, the inner covering film is relatively soft, which can help the inner stent to conform to a tortuous vascular morphology; meanwhile, the resilience of the inner covering film is small, so that the inner covering film can be deformed more easily in the lumen; when the inner stent is implanted at a lesion position, the inner covering film can be expanded to a certain extent under the impact of blood flow on the inner stent, so that the inner stent can be better attached to the wall, and blood is prevented from flowing to the lesion position from the outer side of the inner stent; in addition, the resilience of the outer stent is larger, and after the covered stent is released, the outer covering film can rebound quickly, which helps the outer stent to properly fill the gap between the inner stent and the wall of the lumen, so as to effectively prevent inner leakage.

A covered stent, comprises
a radially compressible inner stent, wherein the inner stent includes an inner support skeleton and an inner covering film arranged on the inner support skeleton; and
an outer stent surrounding the inner stent, wherein the outer stent covers at least part of the inner stent, the outer stent includes an outer support skeleton and an outer covering film arranged on the outer support skeleton, one end of the outer covering film is hermetically connected to the inner covering film, and the light transmittance of the outer covering film is greater than that of the inner covering film.

A preparation method for the covered stent, wherein the method comprises:
fixing an outer stent to an inner stent, and fixing the inner stent to a mold;
wrapping the surface of the inner stent and the surface of the outer stent with a thermal conduction material, wherein the thickness of the thermal conduction material wrapped on the surface of the inner stent is greater than that of the thermal conduction material wrapped on the surface of the outer stent;
arranging a thermal insulation material between the outer stent and the inner stent; and
compressing, heating and cooling the whole assembly to obtain the covered stent.

For the above covered stent, by providing light transmittance of the outer covering film that is greater than that of the inner covering film, with the light transmittance of the inner covering film being lower, and the microscopic fiber structure of the inner covering film being relatively complete, so that the inner covering film has good biocompatibility, and facilitates the crawling of cells after implantation; meanwhile, the inner stent can also have good elasticity, which is helpful to the curving deformation of the inner stent to improve the compliance and wall attachment of the inner stent; the light transmittance of the outer covering film is higher, so that the outer covering film is smoother than the inner stent; after being mounted in a sheath, the outer covering film is less prone to mutual adhesion, which is beneficial to reducing the release resistance of the covered stent; and the outer covering film can be more easily restored to the original size after being released, so as to plug the gap with the wall of the lumen.

A covered stent, comprises
a radially compressible inner stent, wherein the inner stent includes an inner support skeleton and an inner covering film arranged on the inner support skeleton; and
an outer stent surrounding the inner stent, wherein the outer stent covers at least part of the inner stent, the outer stent includes an outer support skeleton and an outer covering film arranged on the outer support skeleton, one end of the outer covering film is hermetically connected to the inner covering film, the tensile strength of the outer covering film is greater than that of the inner covering film, and the elongation of the outer covering film is smaller than that of the inner covering film.

According to the covered stent, by providing that the tensile strength of the outer covering film of the outer stent is greater than that of the inner covering film of the inner stent, the outer covering film can be prevented from breaking during loading or releasing, and the risk of failure of the covered stent can be reduced. The tensile strength of the inner covering film is smaller, i.e. under the same conditions and under tension smaller than the tensile strength force; the deformation of the inner covering film may be larger, so that the inner covering film can better conform to a curved vascular morphology. By providing the outer covering film with a smaller elongation than that of the inner covering film, the elongation of the inner covering film is larger, so that the inner covering film can properly deform and expand under the action of blood pressure after the covered stent is released, so that the inner stent can be better attached to the wall of a blood vessel, and reduce the probability of inner leakage; and the elongation of the outer covering film is smaller, so that the outer covering film is less prone to deformation during loading and releasing.

DETAILED DESCRIPTION OF THE INVENTION

In order to make the above objects, features and advantages of the present disclosure easier to understand, specific embodiments of the present disclosure will be described in detail below in conjunction with the accompanying drawings. In the following description, numerous specific details are illustrated for full understanding of the present disclosure. However, the present disclosure can be implemented by other means different from those described here, a person skilled in the art may make similar improvements without departing from the essence of the present disclosure, and therefore, the present disclosure is not limited to the specific embodiments disclosed below.

It should be noted that when one element is "fixed" or "arranged" on other element, the element may be directly located on the other element or a medium element may exist. When one element is considered to be "connected" to other element, the element may be directly connected to the other element or a medium element may exist simultaneously. The terms "vertical", "horizontal", "left", "right" and the like used herein are for illustrative purposes only, and are not meant to be the only embodiments.

Unless otherwise defined, all technological and scientific terms used herein have the same meanings as commonly understood by those of ordinary skill in the technical field of the present disclosure. The terms used in the description of the present disclosure are only for the purpose of describing specific embodiments, but are not intended to limit the present disclosure. The term "and/or" used herein includes any one or all of the combinations of one or more relevant items listed.

For the convenience of description, a lumen is illustrated in terms of a blood vessel, and the blood vessel may be an aortic arch, or a thoracic aorta, or an abdominal aorta. It should be appreciated by a person of ordinary skill in the art that the blood vessel is described by way of example only and does not limit the present disclosure. The solutions of the present disclosure are applicable to various human lumens, for example, digestive tract lumens. Various modifications and variations taught by the present disclosure are all within the protection scope of the present disclosure. Additionally, in the description of the blood vessel, the orientation may be defined in terms of a direction of blood flow, and it is defined in the present disclosure that blood flows from a proximal end to a distal end.

Figure 1:
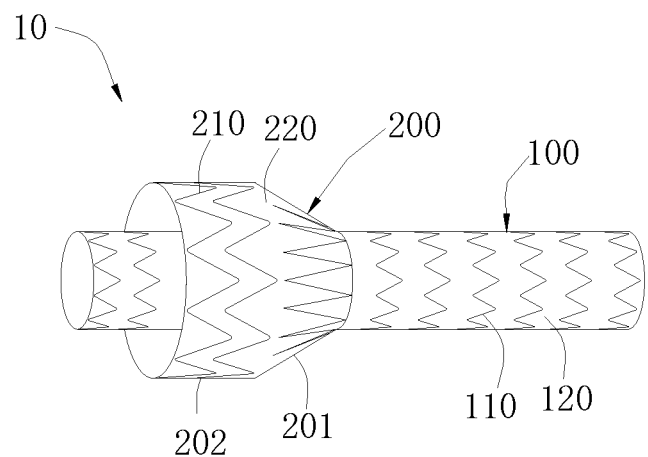
FIG. 1 is a schematic structural diagram of a covered stent according to an embodiment of the present application.

Referring to FIG. 1, a covered stent 10 of the present disclosure includes an inner stent 100 and an outer stent 200, the outer stent 200 is coupled to the inner stent 100 to surround the inner stent 100, the outer stent 200 covers at least part of the inner stent 100, and one end of the outer stent 200 is hermetically connected to the inner stent 100.

Specifically, the inner stent 100 and the outer stent 200 each have a radial compression capability, can be compressed under the action of an external force, and can be self-expanded or expanded by a machine (for example, expanded by a balloon) after the external force is removed, to restore to an original shape and maintain the original shape, so that the inner stent 100 and the outer stent 200 can be closely attached to the wall of a lumen through a radial support force thereof after being implanted into the lumen. The inner stent 100 is of a lumen structure with two open ends and a closed middle. The inner stent 100 can be used as a new fluid passage after being implanted into the lumen, for example, as a new blood flow passage after being implanted into a blood vessel. One end of the outer stent 200 is hermetically connected to an outer circumferential surface of the inner stent 100 to form a closed orifice, and the other end is open. The outer stent 200 can automatically expand after being released to fill the gap between the inner stent 100 and the wall of the lumen.

Figure 2:
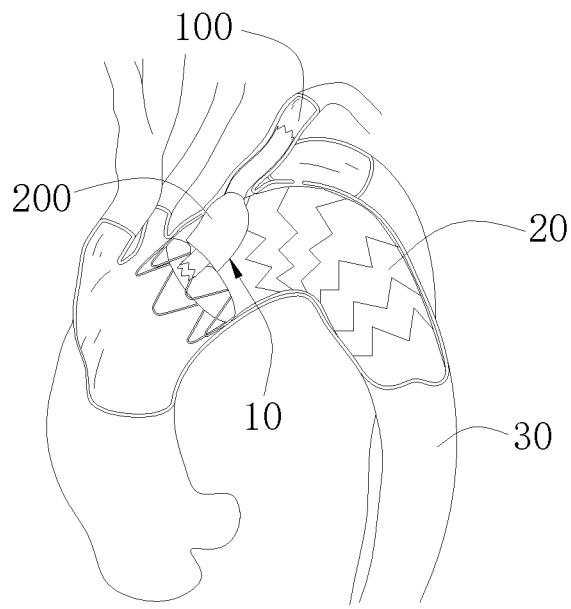
FIG. 2 is a schematic structural diagram showing that the covered stent shown in FIG. 1 cooperates with a main stent and is implanted into a blood vessel.

The covered stent 10 may be used for the reconstruction of a branch vessel in a chimney technique. Refer to FIG. 2, which is a schematic structural diagram showing that the covered stent 10 as a branch stent cooperates with a main stent 20. After implantation, the orientations of proximal end openings of the covered stent 10 and the main stent 20 are identical, and the covered stent 10 and the main stent 20 are arranged side by side in a main vessel 30. A proximal end surface of the outer stent 200 of the covered stent 10 can be at least partially flush with a proximal end surface of the main stent 20, a proximal end surface of the inner stent 100 extends out of the main stent 20, a distal end of the inner stent 100 is placed in the branch vessel for anchoring, and blood flow can enter the branch vessel through a duct built by the inner stent 100, so as to achieve the effect of reconstructing the branch vessel. During the pulsating contraction of the main vessel 30, proximal end regions of the covered stent 10 and the main stent 20 radially squeeze each other in the main vessel 30, and the outer stent 200 can follow the morphologies of the vessel wall and the main stent 20 to deform, thus forming a cavity between the outer stent 200 and the inner stent 100. Blood flowing into the cavity can serve as a filling material to plug an I-type inner leakage passage, which prevents the blood flow from entering a tumor or a dissection, and ensures that the inner stent 100 is smooth and the blood can smoothly flow into the branch vessel. It should be known that the covered stent 10 may be used not only with the main stent 20, but also alone.

In the illustrated embodiment, the outer stent 200 includes a tapered section 201 and a straight section 202 connected to the tapered section 201, and the end of the tapered section 201 away from the straight section 202 is connected to the inner stent 100. One end of the tapered section 201 is hermetically connected to the inner stent 100, and the other end is radially expanded outwardly in a direction from a distal end to a proximal end to form an approximately tapered structure. The straight section 202 is connected to the proximal end of the tapered section 201 and arranged parallel to the inner stent 100. In order to improve the plugging effect of the outer stent 200, the diameter of the straight section 202 is not less than 1.5 times the diameter of the inner stent 100, so that the outer stent can be properly attached to the wall of the lumen and deform in accordance with an external force to effectively prevent an I-type inner leakage. In an embodiment, the diameter of the straight section 202 is not less than twice the diameter of the inner stent 100.

With continued reference to FIG. 1, the inner stent includes an inner support skeleton 110 and an inner covering film 120 arranged on the inner support skeleton 110, and the inner support skeleton 110 cooperates with the inner covering film 120 to form a side wall of the inner stent 100. The outer stent 200 includes an outer support skeleton 210 and an outer covering film 220 arranged on the outer support skeleton 210. In an embodiment, the radial support force of the outer support skeleton 210 is smaller that of the inner support skeleton 100. Because the radial support force of the outer support skeleton 210 is small, the outer stent 200 is easily deformable along with the inner wall of the lumen, thereby avoiding the formation of a gap between the outer stent 200 and the inner wall of the lumen, and therefore effectively avoiding the I-type inner leakage. In addition, the radial support force of the inner support skeleton 110 is large, and the inner stent 100 can be closely attached to the wall of the lumen, so that the whole covered stent 10 is fixed in the lumen, and is prevented from being displaced or separated from the lumen.

Both the inner support skeleton 110 and the outer support skeleton 210 can be made of various biocompatible materials, including known materials used in the manufacturing of implantable medical devices or combinations of various materials, such as 316L stainless steel, cobalt-chromium-nickel-molybdenum-iron alloy, nickel-titanium alloy (nitinol), or other biocompatible metals. Both the inner support skeleton 110 and the outer support skeleton 210 can be formed by braided metal wires or cut from metal tubes. For example, the inner support skeleton 110 and the outer support skeleton 210 each may include a plurality of turns of woven wave rings in the axial direction, such as multiple turns of zigzag waves; or include a spiral wound structure; or include a net structure formed by braided metal wires, or a cut net structure cut from metal tubes. A suitable inner support skeleton and outer support skeleton may be selected by a person of ordinary skill in the art as required, and details are not described herein again. In this embodiment, both the inner support skeleton 110 and the outer support skeleton 210 are woven from nickel-titanium wires. The diameter of the nickel-titanium wires used for the outer support skeleton 210 is smaller than that of the nickel-titanium wires used for the inner support skeleton 110, which is beneficial to reducing the size of a sheath required for the covered stent 10.

Both the outer covering film 220 and the inner covering film 120 are PTFE films, the inner covering film 120 wraps the inner support skeleton 110 by means of hot melting, the outer covering film 220 wraps the outer support skeleton 210 by means of hot melting, and the outer covering film 200 is connected to an outer surface of the inner covering film 120 by means of hot melting.

The light transmittance of the outer covering film 220 is greater than that of the inner covering film 120. The light transmittance is related to the microscopic characteristics of the film material. Taking PTFE as an example, the light transmittance of a raw PTFE film material is relatively low. If the light transmittance of a finished film material after processing is lower, the surface characteristics thereof are closer to those of the raw material, that is, the microscopic fiber structure is more complete, and a finished film product is softer and more easily deformable and has a certain viscosity. With the strengthening of process conditions (for example, the increase of heating time), the surface fiber structure of the film material is fused, the light transmittance of the finished film material is further increased, different physical characteristics are embodied, and the finished film product is harder and smoother but cannot be stretched. By providing the light transmittance of the outer covering film 220 to be greater than that of the inner covering film 120, the light transmittance of the inner covering film 120 is lower, and the microscopic fiber structure of the inner covering film 120 is relatively complete, so that the inner covering film 120 has good biocompatibility, and facilitates cells to crawl after implantation; meanwhile, the inner covering film 120 can also have good elasticity, which is helpful to the curving deformation of the inner stent 100 to improve the compliance and wall attachment of the inner stent 100; the light transmittance of the outer covering film 220 is higher, so that the outer covering film 220 is smoother than the inner covering film 120; after being mounted in a sheath, the outer covering film 220 is less prone to mutual adhesion, which is beneficial to reducing the release resistance of the covered stent 10; and the outer covering film 220 can be more easily restored to the original size after being released, to plug the gap with the wall of the lumen. Of course, in other embodiments, the outer covering film 220 and the inner covering film 120 are also not limited to PTFE films, but may be other materials having similar properties to PTFE.

In the present application, the light transmittance is the ratio of the luminous flux transmitted through an object to the luminous flux irradiated to the object; that is, when the intensity $I_0$ of incident light is constant, if the intensity $I_a$ of light absorbed by a medium is larger, the intensity $I_t$ of the transmitted light is smaller, and the ability of the light to transmit through the medium, referred to as the light transmittance, is expressed by $I_t/I_0$, i.e. $T=I_t/I_0$. The light transmittance in the present application can be tested by using a spectrophotometer.

In an embodiment, the light transmittance of the inner covering film 120 is less than 50%, and the light transmittance of the outer covering film 220 is 50% to 70%, which can help the inner stent 100 to properly conform to a tortuous vascular anatomic form, and ensures the long-term smoothness of the covered stent 10. The surface of the outer covering film 220 is smooth, which can reduce the release resistance of the covered stent 10. In addition, the outer covering film 220 is easy to expand after being released, which can effectively prevent inner leakage.

In an embodiment, the thickness of the outer covering film 220 is smaller than that of the inner covering film 120, which can reduce the size of the sheath required for the covered stent 10. Specifically, the outer covering film 220 has a thickness of 10 µm to 50 µm, and the inner covering film 120 has a thickness of 20 µm to 70 µm. In an embodiment, the light transmittance of the inner covering film 120 is 30% to 48% and the thickness of the inner covering film 120 is 20 µm to 30 µm, and the light transmittance of the outer covering film 220 is 60% to 70% and the thickness of the outer covering film 220 is 15 µm to 25 µm.

The present disclosure further provides a preparation method of the covered stent 10, including:

S11, the outer stent 200 is fixed to the inner stent 100, and the inner stent 100 is fixed to a mold 40.

Figure 3:
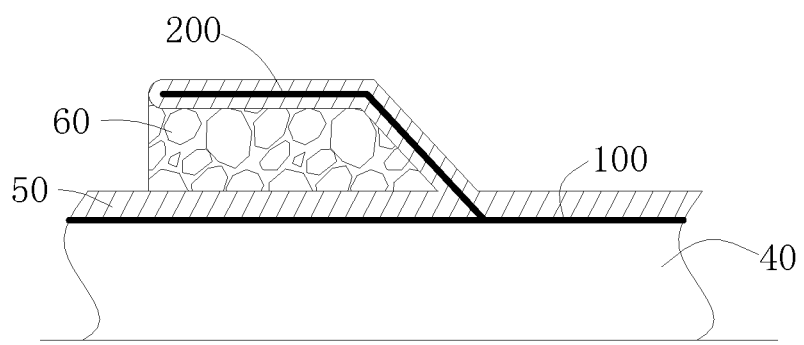
FIG. 3 is a schematic diagram of the covered stent shown in FIG. 1 during preparation.

Specifically, referring also to FIG. 3, the outer support skeleton 210 is fixed to the inner support skeleton 120, inner and outer surfaces of the outer support skeleton 210 are covered with the outer covering film 220, inner and outer surfaces of the inner support skeleton 110 are covered with the inner covering film 120, and the inner support skeleton 110 is wrapped around the mold 40. The mold 40 may be a glass or metal fixture.

S12, the surface of the inner stent 100 and the surface of the outer stent 200 are wrapped with a thermal conduction material 50, wherein the thickness of the thermal conduction material 50 wrapped on the surface of the inner stent 100 is greater than that of the thermal conduction material 50 wrapped on the surface of the outer stent 200.

Specifically, referring also to FIG. 3, the inner and outer surfaces of the outer stent 200 are wrapped with the thermal conduction material 50, and the outer surface of the inner stent 100 is wrapped with the thermal conduction material 50, wherein the thickness of the thermal conduction material on the surface of the inner stent 100 is greater than that of the heat conducting material on the surfaces of the outer stent 200, thereby lowering the heat treatment temperature of the inner stent 100, achieving little fiber structure damage and achieving a low light transmittance.

S13, a thermal insulation material 60 is arranged between the outer stent 200 and the inner stent 100.

In this embodiment, the thermal insulation material 60 may be a filler such as tin foil paper, aluminum foil paper, thermal insulation sand or powder. Different heat treatment temperatures for the inner stent 100 and the outer stent 200 are achieved through the thermal insulation material.

S14, the whole assembly is compressed, heated and cooled to obtain the covered stent 10.

In this embodiment, the heating temperature is 400° C. to 450° C. If the temperature is too low, the heat treatment is insufficient, and the film material cannot be bonded. If the temperature is too high, fibers are completely destroyed, and the elasticity and toughness of the covering film are lost. The whole assembly is held for more than 20 minutes at this temperature, and then rapidly cooled to room temperature. It should be noted that, in other embodiments, suitable temperature and holding time can be selected according to specific requirements.

Figure 4:
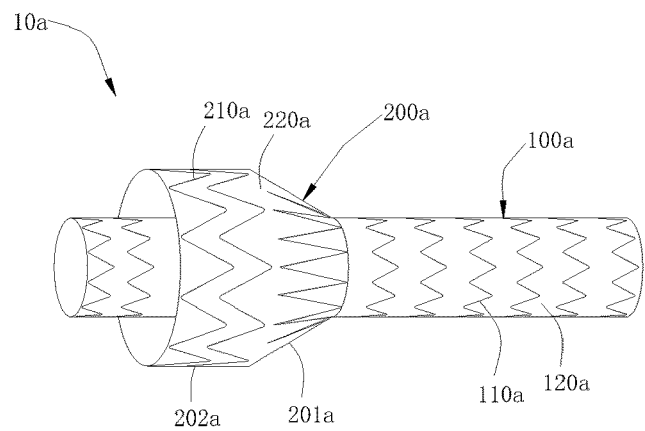
FIG. 4 is a schematic structural diagram of a covered stent according to another embodiment of the present application.

Referring to FIG. 4, a covered stent 10a according to another embodiment of the present disclosure includes an inner stent 100a and an outer stent 200a, the outer stent 200a is coupled to and surrounds the inner stent 100a, the outer stent 200a covers at least part of the inner stent 100a, and one end of the outer stent 200a is hermetically connected to the inner stent 100a.

Specifically, the inner stent 100a and the outer stent 200a each have a radial compression capability, can be compressed under the action of an external force, and can self-expand or restore to an original shape and maintain the original shape by mechanical expansion (for example, expanded by a balloon) after the external force is removed, so that the inner stent 100a and the outer stent 200a can be closely attached to the wall of a lumen through a radial support force thereof after being implanted into the lumen. The inner stent 100a is of a lumen structure with two open ends and a closed middle. The inner stent 100a can be used as a new fluid passage after being implanted into the lumen, for example, as a new blood flow passage after being implanted into a blood vessel. One end of the outer stent 200a is hermetically connected to an outer circumferential surface of the inner stent 100a to form a closed orifice, and the other end is open. The outer stent 200a can automatically expand after being released to fill the gap between the inner stent 100a and the wall of the lumen.

Figure 5:
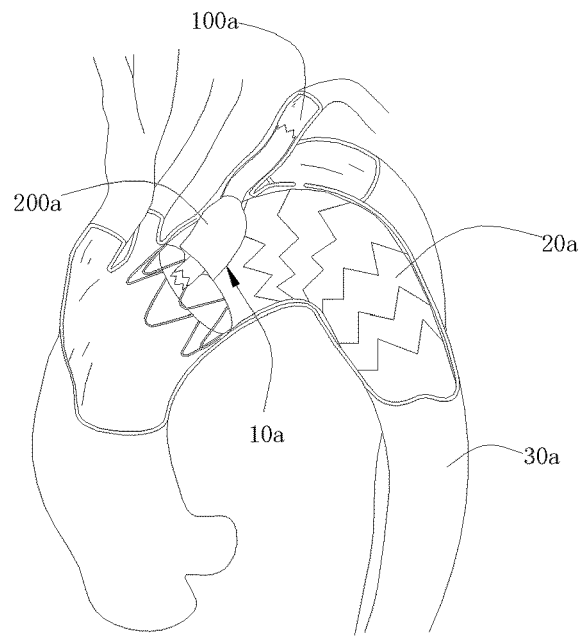
FIG. 5 is a schematic structural diagram showing that the covered stent shown in FIG. 4 cooperates with a main stent and is implanted into a blood vessel.

The covered stent 10a may be used for the reconstruction of a branch vessel in a chimney technique. Refer to FIG. 5, which is a schematic structural diagram showing that the covered stent 10a as a branch stent cooperates with a main stent 20a. After implantation, the orientations of proximal end openings of the covered stent 10a is consistent with that of the main stent 20a, and the covered stent 10a and the main stent 20a are arranged side by side in a main vessel 30a. A proximal end surface of the outer stent 200a of the covered stent 10 can be at least partially flush with a proximal end surface of the main stent 20a, a proximal end surface of the inner stent 100a extends out of the main stent 20a, a distal end of the inner stent 100a is placed in the branch vessel for anchoring, and blood flow can enter the branch vessel through a duct built by the inner stent 100a, so as to achieve the effect of reconstructing the branch vessel. During the pulsating contraction of the main vessel 30a, proximal end regions of the covered stent 10a and the main stent 20a radially squeeze each other in the main vessel 30a, and the outer stent 200a can follow the morphologies of the vessel wall and the main stent 20a to deform, thus forming a cavity between the outer stent 200a and the inner stent 100a. Blood flowing into the cavity can serve as a filling material to plug an I-type inner leakage passage, which prevents the blood flow from entering a tumor or a dissection, and ensures that the inner stent 100a is smooth and the blood can flow smoothly into the branch vessel. It should be known that the covered stent 10a may be used not only with the main stent 20a, but also alone.

In the illustrated embodiment, the outer stent 200a includes a tapered section 201a and a straight section 202a connected to the tapered section 201a, and the end of the tapered section 201a away from the straight section 202a is connected to the inner stent 100a. One end of the tapered section 201a is hermetically connected to the inner stent 100a, and the other end is radially expanded outward in a direction from a distal end to a proximal end to form an approximately tapered structure. The straight section 202a is connected to the proximal end of the tapered section 201a and arranged parallel to the inner stent 100a. In order to improve the plugging effect of the outer stent 200a, the diameter of the straight section 202a is not less than 1.5 times the diameter of the inner stent 100a, so that the outer stent can be well attached to the wall of the lumen and deform in accordance with an external force to well prevent an I-type inner leakage. In an embodiment, the diameter of the straight section 202a is not less than twice the diameter of the inner stent 100a.

With continued reference to FIG. 4, the inner stent includes an inner support skeleton 110a and an inner covering film 120a arranged on the inner support skeleton 110a, and the inner support skeleton 110a cooperates with the inner covering film 120a to form a side wall of the inner stent 100a. The outer stent 200a includes an outer support skeleton 210a and an outer covering film 220a arranged on the outer support skeleton 210a. In an embodiment, the radial support force of the outer support skeleton 210a is smaller that of the inner support skeleton 100a. Because the radial support force of the outer support skeleton 210a is small, the outer stent 200a is easily deformable along with the inner wall of the lumen, thereby avoiding the formation of a gap between the outer stent 200a and the inner wall of the lumen, and effectively avoiding the I-type inner leakage. In addition, the radial support force of the inner support skeleton 110a is large, and the inner stent 100 can be closely attached to the wall of the lumen, so that the whole covered stent 10a is fixed in the lumen, and is prevented from being displaced or separated from the lumen.

Both the inner support skeleton 110a and the outer support skeleton 210a can be made of various biocompatible materials, including known materials used in the manufacturing of implantable medical devices or combinations of various materials, such as 316L stainless steel, cobalt-chromium-nickel-molybdenum-iron alloy, nickel-titanium alloy (nitinol), or other biocompatible metals. Both the inner support skeleton 110a and the outer support skeleton 210a can be formed by braided metal wires or cut from metal tubes. For example, the inner support skeleton 110a and the outer support skeleton 210a each may include a plurality of turns of woven wave rings in the axial direction, such as multiple turns of zigzag waves; or include a spiral wound structure; or include a net structure formed by braided metal wires, or a cut net structure cut from metal tubes. A suitable inner support skeleton and outer support skeleton may be selected by a person of ordinary skill in the art as required, and details are not described herein again. In this embodiment, both the inner support skeleton 110a and the outer support skeleton 210a are woven from nickel-titanium wires. The diameter of the nickel-titanium wires used for the outer support skeleton 210a is smaller than that of the nickel-titanium wires used for the inner support skeleton 110a, which is beneficial to reducing the size of a sheath required for the covered stent 10a.

Both the outer covering film 220a and the inner covering film 120a are PTFE films, the inner covering film 120a wraps the inner support skeleton 110a by means of hot melting, the outer covering film 220a wraps the outer support skeleton 210a by means of hot melting, and the outer covering film 200a is hermetically connected to an outer surface of the inner covering film 120a by means of hot melting. Of course, in other embodiments, the outer covering film 220a and the inner covering film 120a may also not be limited to PTFE films, but may be other materials having similar properties to PTFE.

Figure 6:
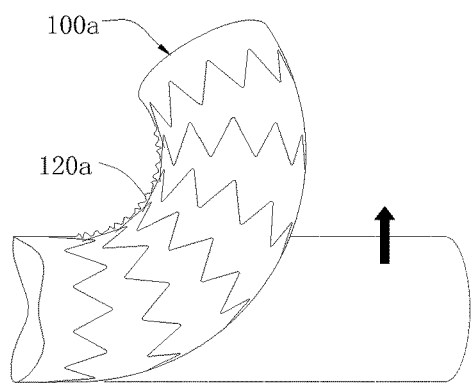
FIG. 6 is a schematic structural diagram of an inner stent shown in FIG. 4 from a natural state to a curved state.

The resilience of the outer covering film 220a is greater than that of the inner covering film 120a. Referring to FIG. 6, when the inner stent 100a is axially compressed or bends, the inner covering film 120a is wrinkled; because the resilience of the inner covering film 120a is smaller, and the straightening force (i.e. the force for restoring from a curved state to a natural state) of the inner stent 100a is smaller, the stimulation of the inner stent 100a to the wall of the lumen can be reduced; in addition, the inner covering film 120a is relatively soft, which can help the inner stent to properly conform to a tortuous vascular morphology; meanwhile, the resilience of the inner covering film 120 is small, so that the inner covering film 120a can be deformed more easily in the lumen; when the inner stent 100a is implanted at a lesion position, the inner covering film 120a can be expanded to a certain extent under the impact of blood flow on the inner stent, so that the inner stent 100 can be better attached to the wall, and blood is prevented from flowing to the lesion position from the outer side of the inner stent 100a; in addition, the resilience of the outer stent 220a is large, and after the covered stent 10a is released, the outer covering film 220a can rebound quickly, which helps the outer stent 200a to effectively fill the gap between the inner stent 120a and the wall of the lumen, so as to effectively prevent inner leakage.

In the present application, the resilience is measured on the inner covering film 120a and the outer covering film 220a respectively at 20° C. by means of a Schob pendulum according to DIN 53512. During measurement, the inner covering film 120a and the outer covering film 220a are respectively placed on the surface of a plastic test piece having a thickness of 12.5 mm and a resilience of 24%.

In an embodiment, the resilience of the inner covering film 120a is 10% to 15%, and the resilience of the outer covering film 220a is 15% to 20%, which can help the inner stent 100a to properly conform to a tortuous vascular anatomic form, and ensures the long-term smoothness of the covered stent 10a. In addition, the outer covering film 220a is easy to expand after being released, which can effectively prevent inner leakage.

Figure 7:
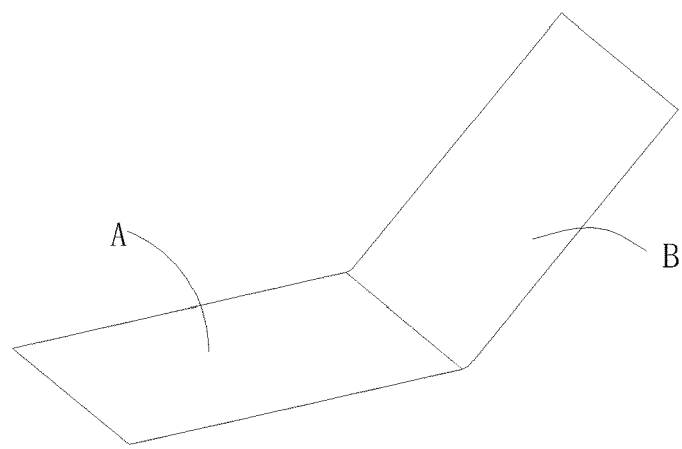
FIG. 7 is a schematic structural diagram of an inner covering film or an outer covering film during testing.

In an embodiment, the inner covering film 120a and the outer covering film 220a are tested by the following method: referring to FIG. 7, a rectangular inner covering film 120a and a rectangular outer covering film 220a of the same size (e.g. 20 to 10 mm) are respectively taken, and each covering film is divided into an area A and an area B along its middle line of the long side, then each covering film is folded along its middle line of the long side until the area A coincides with the area B, and each covering film is stood for natural restoration until the angle between the area A and the area B does not change. The angle between the area A and the area B in the outer covering film 220a is between 120° to 150°, the angle between the area A and the area B in the inner covering film 120a between is 90° to 130°, and the angle between the area A and the area B in the outer covering film 220a is greater than the angle between the area A and the area B in the inner covering film 120a. In this way, after the outer stent 200a is released, the outer covering film 220a can be quickly rebounded to fill the gap between the inner stent 100a and the wall of the lumen, since the covering and releasing of the outer stent 200a would not be difficult due to having too large of an angle, while the inner covering film 120a can effectively expand after being released, and does not produce a large straightening force due to having too large of an angle.

In an embodiment, the thickness of the outer covering film 220a is smaller than that of the inner covering film 120a, which can reduce the size of the sheath required for the covered stent 10a. Specifically, the thickness of the outer covering film 220a is 10 μm to 50 μm, and the thickness of the inner covering film 120a is 20 μm to 70 μm. In an embodiment, the thickness of the inner covering film 120a is 20 to 30 μm, and the thickness of the outer covering film 220a is 15 μm to 25 μm.

The present application further provides a preparation method of the covered stent 10a, including:

S11a, the outer stent 200a is fixed to the inner stent 100a, and the inner stent 100a is fixed to an inner mold 40a.

Specifically, referring also to FIG. 5, the outer support skeleton 210a is fixed to the inner support skeleton 120a, inner and outer surfaces of the outer support skeleton 210a are covered with the outer covering film 220a, inner and outer surfaces of the inner support skeleton 110a are covered with the inner covering film 120a, and the inner support skeleton 110a is wrapped around the inner mold 40a. The inner mold 40a may be a glass or metal fixture.

S12a, an outer mold 50a is wrapped around the inner stent 100a, and the outer mold 50a covers the outer surface of the outer stent 200a, wherein the thermal conductivity of the outer mold 50a is smaller than that of the inner mold 40a, or the thickness of the outer mold 50a is greater than that of the inner mold 40a; and the outer mold 50a is fully attached to the inner mold 40a.

Figure 8:
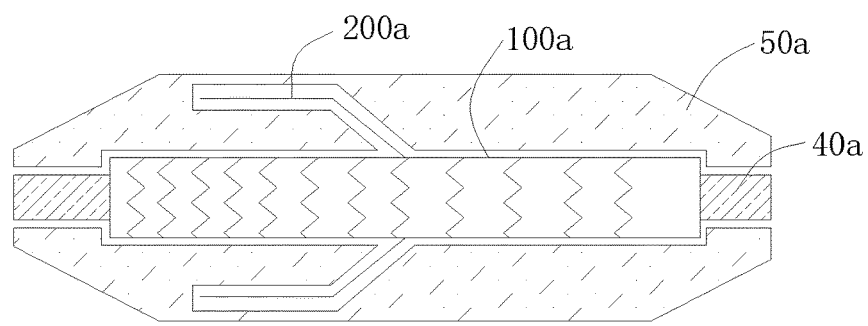
FIG. 8 is a schematic diagram of the covered stent shown in FIG. 4 during preparation.

Specifically, referring also to FIG. 8, the inner and outer surfaces of the outer stent 200a are wrapped by the outer mold 50a, and the outer surface of the inner stent 100a is also covered by the outer mold 50a, wherein the thermal conductivity of the outer mold 50a is smaller than that of the inner mold 40a, or the thickness of the outer mold 50a is greater than that of the inner mold 40a.

S13a, the whole assembly as described above is compressed, heated and held for a period of time, the outer mold 50a is opened, and the whole assembly is naturally cooled to room temperature to obtain the covered stent 10a.

In this embodiment, the heating temperature is 400° C. to 450° C. If the temperature is too low, the heat treatment is insufficient, and the film material cannot be bonded. If the temperature is too high, the elasticity and toughness of the covering film are lost. The whole assembly is held for more than 30 minutes at this temperature, and then naturally cooled to room temperature. I, should be noted that, in other embodiments, suitable temperature and holding time can be selected according to specific requirements.

Figure 9:
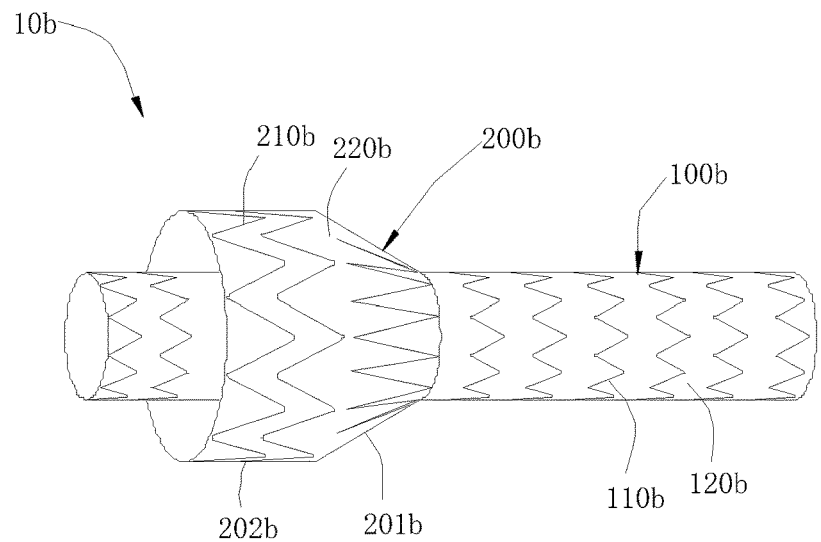
FIG. 9 is a schematic structural diagram of a covered stent according to still another embodiment of the present application.

Referring to FIG. 9, a covered stent 10b according to still another embodiment of the present disclosure includes an inner stent 100b and an outer stent 200b, the outer stent 200b is coupled to and surrounds the inner stent 100b, the outer stent 200b covers at least part of the inner stent 100b, and one end of the outer stent 200b is hermetically connected to the inner stent 100b.

Specifically, the inner stent 100b and the outer stent 200b each have a radial compression capability, can be compressed under the action of an external force, and can self-expand or restore to an original shape and maintain the original shape by mechanical expansion (for example, expanded by a balloon) after the external force is removed, so that the inner stent 100b and the outer stent 200b can be closely attached to the wall of a lumen through a radial support force thereof after being implanted into the lumen. The inner stent 100b is of a lumen structure with two open ends and a closed middle. The inner stent 100b can be used as a new fluid passage after being implanted into the lumen, for example, as a new blood flow passage after being implanted into a blood vessel. One end of the outer stent 200b is hermetically connected to an outer circumferential surface of the inner stent 100b to form a closed orifice, and the other end is open. The outer stent 200b can automatically expand after being released to fill the gap between the inner stent 100b and the wall of the lumen.

Figure 10:
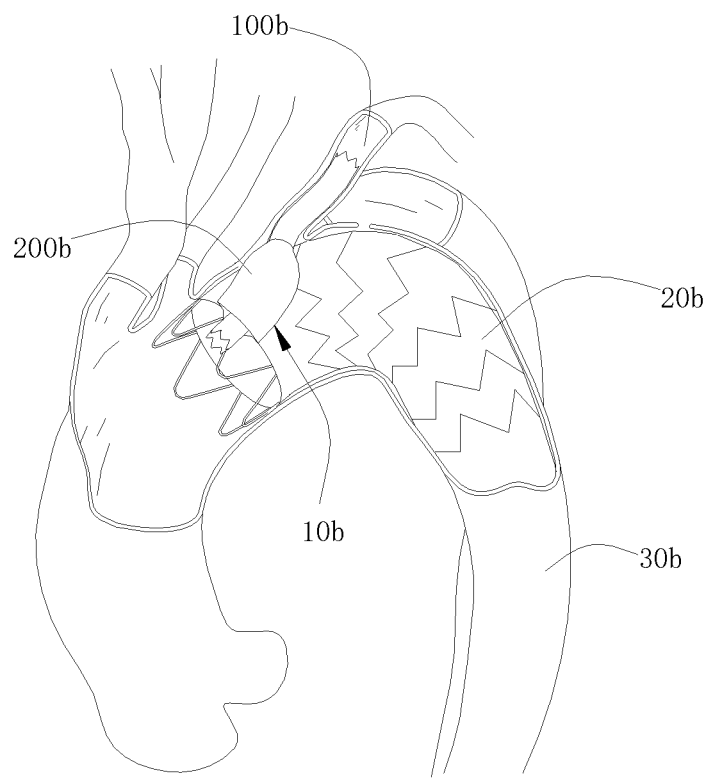
FIG. 10 is a schematic structural diagram showing that the covered stent shown in FIG. 9 cooperates with a main stent and is implanted into a blood vessel.

The covered stent 10b may be used for the reconstruction of a branch vessel in a chimney technique. Refer to FIG. 10, which is a schematic structural diagram showing that the covered stent 10b as a branch stent cooperates with a main stent 20b. After implantation, the orientations of proximal end openings of the covered stent 10b are consistent with that of the main stent 20b, and the covered stent 10b and the main stent 20b are arranged side by side in a main vessel 30b. A proximal end surface of the outer stent 200b of the covered stent 10b can be at least partially flush with a proximal end surface of the main stent 20b, a proximal end surface of the inner stent 100b extends out of the main stent 20b, a distal end of the inner stent 100b is placed in the branch vessel for anchoring, and a blood flow can enter the branch vessel through a duct built by the inner stent 100b, so as to achieve the effect of reconstructing the branch vessel. During the pulsating contraction of the main vessel 30b, proximal end regions of the covered stent 10b and the main stent 20b radially squeeze each other in the main vessel 30b, and the outer stent 200b can follow the morphologies of the vessel wall and the main stent 20b to deform, thus forming a cavity between the outer stent 200b and the inner stent 100b. Blood flowing into the cavity can serve as a filling material to plug an I-type inner leakage passage, which prevents the blood flow from entering a tumor or a dissection, and ensures that the inner stent 100b is smooth and the blood can flow smoothly into the branch vessel. It should be known that the covered stent 10b may be used not only with the main stent 20b, but also alone.

In the illustrated embodiment, the outer stent 200b includes a tapered section 201b and a straight section 202b connected to the tapered section 201b, and the end of the tapered section 201b away from the straight section 202b is connected to the inner stent 100b. One end of the tapered section 201b is hermetically connected to the inner stent 100b, and the other end is radially expanded outwardly in a direction from a distal end to a proximal end to form an approximately tapered structure. The straight section 202b is connected to the proximal end of the tapered section 201b and arranged parallel to the inner stent 100b. In order to improve the plugging effect of the outer stent 200b, the diameter of the straight section 202b is not less than 1.5 times the diameter of the inner stent 100b, so that the outer stent can be well attached to the wall of the lumen and deform in accordance with an external force to well prevent an I-type inner leakage. In an embodiment, the diameter of the straight section 202b is not less than twice the diameter of the inner stent 100b.

With continued reference to FIG. 9, the inner stent includes an inner support skeleton 110b and an inner covering film 120b arranged on the inner support skeleton 110b, and the inner support skeleton 110b cooperates with the inner covering film 120b to form a side wall of the inner stent 100b. The outer stent 200b includes an outer support skeleton 210b and an outer covering film 220b arranged on the outer support skeleton 210b. In an embodiment, the radial support force of the outer support skeleton 210b is smaller that of the inner support skeleton 110b. Because the radial support force of the outer support skeleton 210b is small, the outer stent 200b is easily deformable along with the inner wall of the lumen, thereby avoiding the formation of a gap between the outer stent 200b and the inner wall of the lumen, and effectively avoiding the I-type inner leakage. In addition, the radial support force of the inner support skeleton 110b is large, and the inner stent 100b can be closely attached to the wall of the lumen, so that the whole covered stent 10b is fixed in the lumen, and is prevented from being displaced or separated from the lumen.

Both the inner support skeleton 110b and the outer support skeleton 210b can be made of various biocompatible materials, including known materials used in the manufacturing of implantable medical devices or combinations of various materials, such as 316L stainless steel, cobaltchromium-nickel-molybdenum-iron alloy, nickel-titanium alloy (nitinol), or other biocompatible metals. Both the inner support skeleton 110b and the outer support skeleton 210b can be formed by braided metal wires or cut from metal tubes. For example, the inner support skeleton 110b and the outer support skeleton 210b each may include a plurality of turns of woven wave rings in the axial direction, such as multiple turns of zigzag waves; or include a spiral wound structure; or include a net structure formed by braided metal wires, or a cut net structure cut from metal tubes. Suitable inner support skeleton and outer support skeleton may be selected by a person of ordinary skill in the art as required, and details are not described herein again. In this embodiment, both the inner support skeleton 110b and the outer support skeleton 210b are woven from nickel-titanium wires. The diameter of the nickel-titanium wires used for the outer support skeleton 210b is smaller than that of the nickel-titanium wires used for the inner support skeleton 110b, which is beneficial to reducing the size of a sheath required for the covered stent 10b.

Both the outer covering film 220b and the inner covering film 120b are PTFE films, the inner covering film 120b wraps inner and outer surfaces of the inner support skeleton 110b by means of hot melting, the outer covering film 220b wraps inner and outer surfaces of the outer support skeleton 210b by means of hot melting, and the outer covering film 200b is hermetically connected to an outer surface of the inner covering film 120b by means of hot melting. Of course, in other embodiments, the outer covering film 220b and the inner covering film 120b may also not be limited to PTFE films, but may be other materials having similar properties to PTFE.

Figure 11:
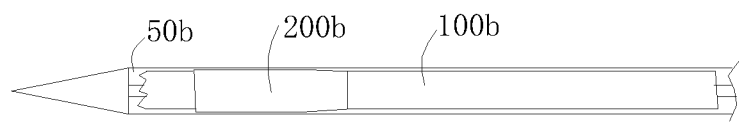
FIG. 11 is a schematic structural diagram after the covered stent shown in FIG. 9 is loaded into a sheath.

The tensile strength of the outer covering film 220b is greater than that of the inner covering film 120b, and the elongation of the outer covering film 220b is smaller than that of the inner covering film 120b. Referring also to FIG. 11, after the covered stent 10b is loaded into a sheath 50b of a delivery device by radial extrusion, since the covered stent 10b is in a radial compression state at this time, the self-expansion tendency of the covered stent 10b inside the sheath 50b results in a large contact area between the outer surface of the covered stent 10b and the inner wall of the sheath 50b, such that the covering film on the outer surface of the covered stent 10b is required to withstand a large frictional force during loading and releasing, while the loading cross-sectional area of the outer stent 200b of the covered stent 10b is at a maximum, and the frictional force borne by the outer covering film 220b of the outer stent 200b is particularly large during assembly and release. By providing that the tensile strength of the outer covering film 220b of the outer stent 200b to be greater than that of the inner covering film 120 of the inner stent 100, the outer covering film 220 is prevented from breaking during loading or releasing, and the risk of failure of the covered stent 10b is reduced. The tensile strength of the inner covering film 120b is smaller, i.e. under the same conditions and under tension smaller than the tensile strength force, so the deformation of the inner covering film 120 may be larger, such that the inner covering film 120b can better conform to a curved vascular morphology. By providing that the elongation of the outer covering film 220b is smaller than that of the inner covering film 120b, the elongation of the inner covering film 120b will also be larger, so that the inner covering film 120b can properly deform and expand under the action of blood pressure after the covered stent 10b is released, such that the inner stent 100b can be better attached to the wall of the blood vessel, and the probability of inner leakage is reduced; and because the elongation of the outer covering film 220b is smaller, the outer covering film 220b is less prone to deformation during loading and releasing.

In the present application, the tensile strength can be tested according to standard YY 0500-2018, and specifically, the testing method is as follows: a sheet-like film material (e.g. 25 mm in width) is axially stretched, and the peak force during stretching to break is recorded.

The elongation can be tested by the following method: for a covered stent with a given specification, the diameter of the covered stent is D1, the covering film is made into a dumbbell-shaped sample with a width of 10 mm at the narrow part, the narrow part is marked with a length L0, a tensile force F=25 kpa*10 mm*D1*0.5≈0.125*D1 newtons is applied to the sample under the condition that the ambient temperature is 37° C.±2° C., the original length L0 of the narrow part is changed to L1 after 48 hours, and the elongation μ=(L1−L0)/L0. The shape of the dumbbell-shaped sample can refer to an I-shaped dumbbell sample in the standard GB/t 528-2009 or ISO 37:2005, and the film thickness of the dumbbell-shaped sample is the same as the film thickness of the covered stent to be tested.

In an embodiment, the tensile strength of the outer covering film 220b is not less than 30 N and an elongation is 5% to 15%. The tensile strength of the inner covering film 120b is not less than 20 N and an elongation is 10% to 30%.

In an embodiment, the material of the outer covering film 220b is the same as that of the inner covering film 120b, and the thickness of the outer covering film 220b is smaller than that of the inner covering film 120b, which can reduce the size of the sheath required for the covered stent 10b. Specifically, the thickness of the outer covering film 220b is 10 μm to 50 μm, and the thickness of the inner covering film 120b is 20 μm to 70 μm. In an embodiment, the thickness of the inner covering film 120b is 20 μm to 30 μm, and the thickness of the outer covering film is 15 μm to 25 μm.

In an embodiment, the peel force of the outer covering film 220b is not smaller than that of the inner covering film 120b. The peel force of the outer covering film 220b is not less than 1 N/mm, which prevents the outer covering film 220b from being separated from the outer support skeleton 210b under the scouring of blood flow, and improves the stability of the covered stent 10b. In the present application, the peel force may be tested by the following method: the sheet-like film material (e.g. 25 mm in width) is peeled by means of a tensile machine, and the force value during peeling is recorded.

The present application further provides a preparation method of the covered stent 10b, including:

S11b, the inner stent 100b is fixed to a mold 40b and heated to a temperature of 290° C. to 300° C., the mold 40 is rotated uniformly in the circumferential direction after the temperature is stabilized, and the inner stent 100b is taken out after a period of time and naturally cooled.

Figure 12:
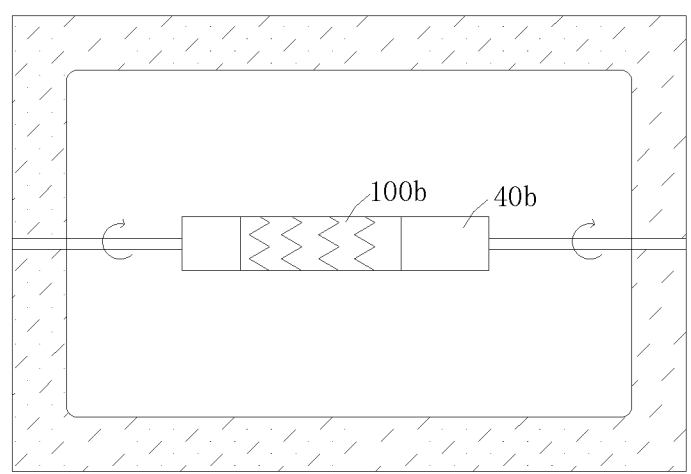
FIG. 12 is a schematic diagram of the covered stent shown in FIG. 9 during preparation.

Specifically, referring also to FIG. 12, the inner and outer surfaces of the inner support skeleton 110b are covered with the inner covering film 120b, and the inner support skeleton 110b is wrapped around on the mold 40b, such that the inner support skeleton 100b is attached to the mold 40b. The mold 40b may be a metal fixture. In an embodiment, the mold 40b is rotated 2-4 revolutions per minute and taken out after 30 minutes of heat preservation.

S12b, the outer stent 200b is fixed to the mold 40b and heated to a temperature of 300° C. to 320° C., the mold 40b is rotated uniformly in the circumferential direction after the temperature is stabilized, and the outer stent 200b is taken out after a period of time and naturally cooled.

Specifically, the inner and outer surfaces of the outer support skeleton 210b are covered with the outer covering film 220b, and the outer support skeleton 210b is wrapped around on the mold 40b, such that the outer support skeleton 210b is attached to the mold 40b. The outer stent 200b and the mold 40b is the same as that of the inner stent 100b and the mold 40b. In an embodiment, the mold 40b is rotated 2-4 revolutions per minute and taken out after 40 minutes of heat preservation.

It should be noted that the shape of the mold 40b may be adjusted according to the shapes of the inner stent 100b and the outer stent 200b.

S13b, the outer stent 200b is fixed to the inner stent 100b to obtain the covered stent 10b.

Specifically, the outer stent 200b can be fixed to the inner stent 100b by means of hot melting or sewing.

The technical features of the above-described embodiments can be combined arbitrarily. For the purpose of simplicity in description, all the possible combinations of the technical features in the above embodiments are not described. However, as long as the combinations of these technical features do not have contradictions, they shall fall within the scope of the specification.

The foregoing embodiments only describe several implementations of the present disclosure, and their descriptions are specific and detailed, but cannot therefore be understood as limitations to the patent scope of the present disclosure. It should be noted that a person of ordinary skill in the art could also make several alterations and improvements without departing from the spirit of the present disclosure and these would all fall within the scope of protection of the present disclosure. Therefore, the protection scope of the present disclosure shall be in accordance with the appended claims.

The invention claimed is:

1. A covered stent, wherein the covered stent comprises a radially compressible inner stent and an outer stent covering the inner stent, the inner stent comprises an inner support skeleton and an inner coating film arranged on the inner support skeleton; and the outer stent covering the inner stent, wherein the outer stent covers at least part of the inner stent, the outer stent comprises an outer support skeleton and an outer coating film arranged on the outer support skeleton, one end of the outer coating film is hermetically connected to the inner coating film; wherein the outer coating film and the inner outer coating film are spaced apart from each other, the outer stent comprises a tapered section and a straight section connected to the tapered section, and one end of the tapered section away from the straight section is hermetically connected to the inner stent, and wherein the hardness of the outer coating film is higher than the inner outer coating film;

wherein the thickness of the outer coating film is smaller than that of the inner coating film; and wherein the thickness of the outer coating film is 10 μm to 50 μm, and the thickness of the inner coating film is 20 μm to 70 μm.

2. The covered stent of claim 1, wherein both the inner coating film and the outer coating film are PTFE films, and the peel force of the outer coating film is not smaller than that of the inner coating film.

3. The covered stent of claim 1, wherein the radial support force of the outer support skeleton is smaller that of the inner support skeleton.

4. The covered stent of claim 1, wherein the diameter of the straight section is not less than 1.5 times the diameter of the inner stent.

5. The covered stent of claim 1, wherein both the inner coating film and the outer coating film are PTFE films, and the peel force of the outer coating film is not smaller than that of the inner coating film.

6. The covered stent of claim 1, wherein the light transmittance of the outer coating film is greater than that of the inner coating film, and wherein light transmittance is defined as the ratio of the luminous flux transmitted through an object to the luminous flux irradiated to the object.

7. The covered stent of claim 6, wherein light transmittance is $T=I_t/I_0$, where $I_t$ is the intensity of transmitted light and $I_a$ is the intensity of light absorbed.

8. The covered stent of claim 1, wherein one end of the outer coating film is connected to the inner coating film, another end of the outer coating film is spaced apart from the inner coating film, a cavity with an opening is defined between the inner coating film and the outer coating film, and the opening faces towards to the proximal end.

* * * * *